US012727976B2

(12) United States Patent
Kim et al.

(10) Patent No.: US 12,727,976 B2
(45) Date of Patent: Sep. 8, 2026

(54) ZIRCONIA SURFACE TREATMENT METHOD

(71) Applicant: AJOU UNIVERSITY INDUSTRY—ACADEMIC COOPERATION FOUNDATION, Suwon-si (KR)

(72) Inventors: Hee-Kyung Kim, Seoul (KR); Chul-Ho Kim, Seoul (KR); Sung Un Kang, Suwon-si (KR); Seung-Joo Kim, Suwon-si (KR); Yu-Kwon Kim, Seoul (KR)

(73) Assignee: AJOU UNIVERSITY INDUSTRY-ACADEMIC COOPERATION FOUNDATION, Suwon-si (KR)

( * ) Notice: Subject to any disclaimer, the term of this patent is extended or adjusted under 35 U.S.C. 154(b) by 19 days.

(21) Appl. No.: 18/861,098

(22) PCT Filed: Mar. 10, 2023

(86) PCT No.: PCT/KR2023/003321
§ 371 (c)(1),
(2) Date: Oct. 28, 2024

(87) PCT Pub. No.: WO2023/210960
PCT Pub. Date: Nov. 2, 2023

(65) Prior Publication Data

US 2025/0352312 A1 Nov. 20, 2025

(30) Foreign Application Priority Data

Apr. 28, 2022 (KR) ........................ 10-2022-0052963

(51) Int. Cl.
*A61C 13/02* (2006.01)
*A61C 8/00* (2006.01)
*A61K 6/818* (2020.01)

(52) U.S. Cl.
CPC ............ *A61C 13/02* (2013.01); *A61C 8/0012* (2013.01); *A61K 6/818* (2020.01)

(58) Field of Classification Search
CPC ........ A61C 13/02; A61C 8/0012; A61K 6/818
(Continued)

(56) References Cited

U.S. PATENT DOCUMENTS 5,783,641 A 7/1998 Koh et al.
2003/0019850 A1* 1/2003 Kensuke .................. C22F 3/00 219/121.61
(Continued)

FOREIGN PATENT DOCUMENTS

CN 113430481 A * 9/2021 ............ C23C 4/134
JP 2022103525 A * 7/2022
(Continued)

OTHER PUBLICATIONS

"Influence of plasma treatment on surface properties of zirconia", J Osaka Dent Univ Oct. 2016 ; 50 (2) : 79-84 https://www.jstage.jst.go.jp/article/jodu/50/2/50_79/_pdf/-char/en.*
(Continued)

*Primary Examiner* — Matthew M Nelson
(74) *Attorney, Agent, or Firm* — ROTHWELL, FIGG, ERNST & MANBECK, P.C.

(57) ABSTRACT

The present invention pertains to a method for treating the surface of 1-5 mol % (preferably, 3 mol %) yttria stabilized zirconia (1-5 mol % (3 mol %) yttria stabilized tetragonal zirconia polycrystal; 3Y-TZP), which is suitable for dental use, with plasma composed of nitrogen and argon mixed gas ($N_2$/Ar). 3Y-TZP treated by the method has excellent anti-
(Continued)

bacterial properties, osseointegration ability, and adhesive performance, and thus has the advantage of being applicable to dental implants etc.

8 Claims, 10 Drawing Sheets

(58) Field of Classification Search
USPC .......................................................... 433/168.1
See application file for complete search history.

(56) References Cited

U.S. PATENT DOCUMENTS

2004/0038555 A1* 2/2004 Sugita .............. H10D 64/01342 257/E21.639
2006/0105297 A1* 5/2006 Knapp ............... A61C 13/0003 433/206
2009/0017087 A1* 1/2009 Byon ..................... C25D 11/26 427/2.27
2011/0269618 A1* 11/2011 Knapp .................. C04B 35/486 501/103
2013/0199361 A1* 8/2013 Lenz ..................... A61L 31/026 428/629
2016/0351376 A1 12/2016 Seok et al.
2017/0159164 A1 6/2017 Huang et al.
2018/0125616 A1* 5/2018 Kitamura .............. C04B 35/486
2019/0046684 A1* 2/2019 Roth ....................... A61L 27/54
2019/0300998 A1 10/2019 Moon et al.
2021/0229315 A1* 7/2021 Lee ......................... B28B 1/001
2022/0068601 A1* 3/2022 Ventzek ............ H01J 37/32357
2022/0359163 A1* 11/2022 Mckenzie ................ C08J 7/123
2023/0066453 A1* 3/2023 Esquivel-Upshaw ........................ A61L 27/54
2024/0392424 A1* 11/2024 Kim ........................ C22F 1/183
2024/0400466 A1* 12/2024 Kim ..................... A61C 8/0013
2025/0069855 A1* 2/2025 Lim ......................... A61C 8/00
2025/0099342 A1* 3/2025 Kim ....................... A61K 6/818
2025/0100944 A1* 3/2025 Kim ........................ C04B 35/48
2025/0352312 A1* 11/2025 Kim ....................... A61C 13/02

FOREIGN PATENT DOCUMENTS

KR 10-1996-0039135 A 11/1996
KR 10-1435158 B1 8/2014
KR 10-2016-0139984 A 12/2016
KR 10-2017-0070814 A 6/2017
KR 10-1853646 B1 5/2018
KR 101993391 B1 * 6/2019 ............ B01J 19/088
KR 10-2019-0113259 A 10/2019
KR 10-2020-0021265 A 2/2020
KR 102390123 B1 * 4/2022 .............. H10P 72/00
KR 20230153130 A * 11/2023 ......... A61C 13/0006
KR 102816359 B1 * 6/2025 ......... A61C 13/0006
TW M409821 U * 8/2011
WO WO-2008009474 A1 * 1/2008 ........... A61C 8/0013
WO WO-2014048585 A1 * 4/2014 ............. A61L 27/06
WO WO-2023210960 A1 * 11/2023 ......... A61C 13/0006
WO WO-2024210330 A1 * 10/2024 ........... A61C 8/0087

OTHER PUBLICATIONS

Influence of plasma treatment on surface properties of zirconia Yuki Ito, Takahisa Okawa, Takamasa Fujii and Masahiro Tanaka (Year: 2016).*
International Search Report of PCT/KR2023/003321 mailed Jun. 20, 2023 (7 pages).
Kang, Sung-Un et al. Effect of the Plasma Gas Type on the Surface Characteristics of 3Y-TZP Ceramic. International Journal of Molecular Sciences. 2022, vol. 23, thesis No. 3007, inner pp. 1-15 (publication: Mar. 10, 2022).

* cited by examiner

B

Total surface free energy ($\gamma^{total}$)
dispersion component($\gamma^{d}$)
polar component ($\gamma^{p}$)

Surface Free Energy (dyne/cm)

50
40
30
20
10
0 a f g
b,c e,f h
b,c d i
b d,e h
c f h control $HeO_2$ $N_2Ar$ $N_2$ Ar

Concentration of N (at%)

2.0
1.8
1.6
1.4
1.2
1.0
0.8
0.6
0.4
0.2
0.0

1.93
1.71
1.31
1.28
0.72 control $HeO_2$ $N_2Ar$ $N_2$ Ar

ZIRCONIA SURFACE TREATMENT METHOD

CROSS-REFERENCE TO RELATED APPLICATIONS

This application is a 35 U.S.C. § 371 National Stage of International Patent Application No. PCT/KR2023/003321, filed Mar. 10, 2023, claiming priority to and the benefit of Korean Patent Application No. 10-2022-0052963, filed on Apr. 28, 2022, the disclosure of which is incorporated herein by reference in its entirety.

TECHNICAL FIELD

The present invention relates to a method for treating the surface of zirconia, and more specifically to a method for treating the surface of zirconia which is stabilized with 1 to 5 mol % (preferably, 3 mol %) of yttria (1 to 5 mol % (3 mol %) yttria stabilized tetragonal zirconia polycrystal; 3Y-TZP) with plasma composed of a mixed gas of nitrogen and argon ($N_2$/Ar), 3Y-TZP having improved biological activity by being surface-treated by the method, and a dental composition including the 3Y-TZP.

BACKGROUND

Meanwhile, the present application was supported by the following national research and development projects.

[National Research and Development Projects Supporting This Invention]

[Project Identification Number]1711144980

[Project Number]2019R1F1A1062112

[Name of Ministry] Ministry of Science and ICT

[Project Management (Specialized) Organization Name] National Research Foundation of Korea

[Research Project Name] Basic Research in Science and Engineering Fields—Basic Research

[Research Project Name] Development of Surface Treatment Technology to Improve the Function of High-Transparency Cubic Zirconia, a New Dental Material

[Project Executing Organization Name] Ajou University Medical Center

[Research Period] Jun. 1, 2019 to Aug. 31, 2022

[Project Identification Number]1465034377

[Project Number] HR21C1003 (HR21C1003010021)

[Name of Ministry] Ministry of Health and Welfare

[Project Management (Specialized) Organization Name] Ministry of Health and Welfare (Korea Health Industry Development Institute)

[Research Project Name] Research-Oriented Hospital Promotion (R&D)

[Research Project Name] Establishment of Quattro Symbiotic Platform Based on Hyper-personalized H-I Future Technology of the 5th Industrial Revolution (Establishment of Early Technology Commercialization Platform for Customized Healing Innovation H-I (Human Interface))

[Project Executing Organization Name] Ajou University Medical Center

[Research Period]Jul. 1, 2021 to Dec. 31, 2029

[Project Unique Number]1711144175

[Project Number]2018R1A2B3009008

[Name of Ministry] Ministry of Science and ICT

[Project Management (Specialized) Organization Name] National Research Foundation of Korea

[Research Project Name] Individual Basic Research (MSIT) (R&D)

[Research Project Name] Development of a Precision-Controlled Treatment Strategy to Overcome Therapy-Resistant Cancer Through Single-Cell Transcriptome-Based Intratumoral Heterogeneity and Tumor Microenvironment Analysis in Refractory Head and Neck Cancer

[Project Executing Organization Name] Ajou University

[Research Period] Mar. 1, 2018 to Feb. 28, 2023

[Project Unique Number]1345334585

[Project Number] NRF-2021R1A6A1A10044950

[Name of Ministry] Ministry of Education

[Project Management (Specialized) Organization Name] National Research Foundation of Korea

[Research Project Name] Establishment of a Research Infrastructure for Science and Engineering—Support for Autonomous Operation Key Research Institutes

[Research Project Name] Basic Science Research Institute

[Project Executing Organization Name] Ajou University

[Research Period] Jun. 1, 2021 to May 31, 2030

[Project Unique Number]1711172489

[Project Number]2022R1F1A1067929

[Name of Ministry] Ministry of Science and ICT

[Project Management (Specialized) Organization Name] National Research Foundation of Korea

[Research Project Name] Basic Research in Science and Engineering Fields—Basic Research

[Research Project Name] Development of Core Technology for Functional Improvement of Dental High Transparency Zirconia through Plasma Ionization Method

[Project Executing Organization Name] Ajou University Medical Center

[Research Period] Jun. 1, 2022 to Feb. 28, 2025

[Project Number]2023R1 A2C3002835

[Name of Ministry] Ministry of Science and ICT

[Project Management (Specialized) Organization Name] Ministry of Science and ICT

[Research Project Name] Mid-Career Researcher Support Project

[Research Project Name] Discovery of Mechanisms Controlling Metabolic Heterogeneity of Cancer and Cancer Microenvironment Based on Transcriptome Profiling in Intractable Head and Neck Cancer and Development of Patient-Tailored Antibody Treatment

[Project Executing Organization Name] Ajou University Medical Center

[Research Period] Mar. 1, 2023 to Feb. 29, 2028

Biomaterials can tune biological interactions by controlling the surface energy, biocompatibility and adhesion strength of a substrate through surface modification strategies. Plasma modification is one method to modify the surface properties of biomaterials through physical collisions of excited gas molecules or high-energy ion bombardment by chemical reactions. Atmospheric-pressure glow discharge (APGD) plasma, particularly cold atmospheric plasma (CAP), has recently attracted much attention in various industrial and medical applications such as surface treatment, film deposition, ozone production for water purification, biomedical decontamination, wound healing, muscle regeneration and anticancer treatment. CAP, which is also called non-thermal plasma (NTP), is composed of partially ionized gases that are not in thermodynamic equilibrium. CAP generates a large amount of reactive oxygen and nitrogen species (RONS) through chemical reactions in biological systems. One common CAP source is the dielectric-barrier discharge (DBD), which operates a self-pulsing plasma with an insulating (dielectric) material in the discharge gap. DBD systems require a high-voltage AC source (1 to 100 kVrms) in the kHz range.

Zirconia (3Y-TZP) ceramics, which are stabilized with 1 to 5 mol % of (approximately 3 mol %) yttria, are widely used in dental application fields for fabricating crowns and bridge restorations, dental implants, orthodontic brackets and root canal posts due to their excellent biocompatibility, sufficient mechanical strength and high esthetics. However, zirconia has a low reactivity and a chemically inert surface, which limits stable bonding with resin cements, cell adhesion or osseointegration. Mechanical surface treatment tends to increase the bonding strength between resin cement and zirconia through micromechanical retention, but it can induce cracks and surface damage, which can worsen the fracture resistance of zirconia. As an alternative to such mechanical surface treatment, plasma treatment of the surface is considered. Plasma surface treatment is performed to increase the surface energy of a material by generating polar groups on the zirconia surface. Although plasma surface treatment has been found to increase the surface hydrophilicity of 3Y-TZP without changing the surface morphology, several studies have shown that plasma treatment did not significantly improve the associated shear bond strength (SBS) between zirconia and composite resin. On the contrary, oxygen radicals generated in plasma can mainly remove organic contaminants on the surface, and exhibit potential antibacterial effects around zirconia.

Nevertheless, plasma performance in various application fields varies greatly depending on experimental parameters. Gas type is one of the important plasma characteristics in plasma performance. Noble gases such as helium (He) or argon (Ar) are generally used to induce CAP discharges because of their low breakdown voltage. However, it has been reported that no chemical reaction was observed in microorganisms with argon gas plasma due to the inert nature of argon in spite of the strong ion bombardment. In contrast, some reactive gases such as oxygen, nitrogen or air can be mixed with noble gases in small amounts to generate chemically active species such as $O_3$, OH, $H_2O_2$, NO and OH radicals at low breakdown voltage and low temperature. In the plasma generated from the mixed gas, the excited noble gases can ionize the reactive gases by energy transfer through collision (Penning ionization), thereby changing the discharge characteristics.

Changes in the electrochemistry of zirconia surfaces increase the bonding efficiency or osseointegration of zirconia implants. The electrical conductivity and quantitative ion concentration were investigated to enhance the reactivity of the zirconia surface during plasma treatment. Recently, it has been reported that the bioactivity and cytocompatibility of 3Y-TZP were enhanced by the creation of new functional groups on the zirconia surface by carbon and nitrogen plasma ion implantation techniques. However, there is no report on plasma-zirconia interaction from the perspective of the role of gas composition in the kinetics of chemical reactions at the surface.

As such, the inventors of the present invention have made efforts to determine the effects of plasma composition on the physicochemical surface modification of 3Y-TZP, and as a result, the inventors of the present invention have determined changes in the surface properties of 3Y-TZP, such as surface energy, surface chemistry, phase composition and morphology, of zirconia specimens that were treated with plasma composed of a $He/O_2$ mixed gas, a $N_2/Ar$ mixed gas, $N_2$ gas or Ar gas through methods such as contact angle, X-ray photoelectron spectroscopy (XPS), X-ray diffraction (XRD) and Rietveld analysis, confocal laser scanning microscopy (CLSM) and scanning electron microscopy (SEM), and have confirmed that the biological activity of zirconia specimens that are treated with plasma composed of a mixed gas of nitrogen and argon ($N_2/Ar$) is significantly improved, thereby completing the present invention.

SUMMARY OF THE INVENTION

An object of the present invention is to provide a method for treating the surface of zirconia.

In order to achieve the above object, the present invention provides a method for treating the surface of zirconia for dental use, including the steps of:

(a) preparing zirconia which is stabilized with 1 to 5 mol % (preferably, 3 mol %) of yttria; and (b) generating plasma composed of a mixed gas of nitrogen and argon ($N_2/Ar$) and irradiating the plasma to the zirconia.

In the present invention, in step (b) above, the plasma may include nitrogen and argon gases at a component ratio of 0.3:9.7 to 1.5:8.5.

In addition, the present invention provides zirconia for dental use whose surface is treated by the above method.

In addition, the present invention provides a dental material, including the zirconia as an active ingredient.

In the present invention, the dental material may be used to manufacture at least one dental article selected from the group consisting of an implant, a crown, an inlay, a post and an orthodontic bracket.

Zirconia (3Y-TZP) which is treated with plasma composed of a mixed gas of nitrogen and argon ($N_2/Ar$) according to the present invention exhibits a significantly decreased contact angle, an increased surface energy, and the highest value of the polar component of the surface energy without a change in surface topography. In addition, the surface oxygen (O) content increases and the surface carbon (C) content decreases, thereby effectively increasing the hydrophilicity of a zirconia surface. Furthermore, when treated with plasma composed of a mixed gas of nitrogen and argon ($N_2/Ar$), the antibacterial properties, osteointegration ability and adhesive performance of 3Y-TZP can be improved by controlling nitrogen functional groups.

BRIEF DESCRIPTION OF THE DRAWINGS

The carbon content in the $N_2/Ar$-treated zirconia was significantly reduced compared to the zirconia treated with plasmas of other types of gases.

DETAILED DESCRIPTION

Figures 1A, 1B:
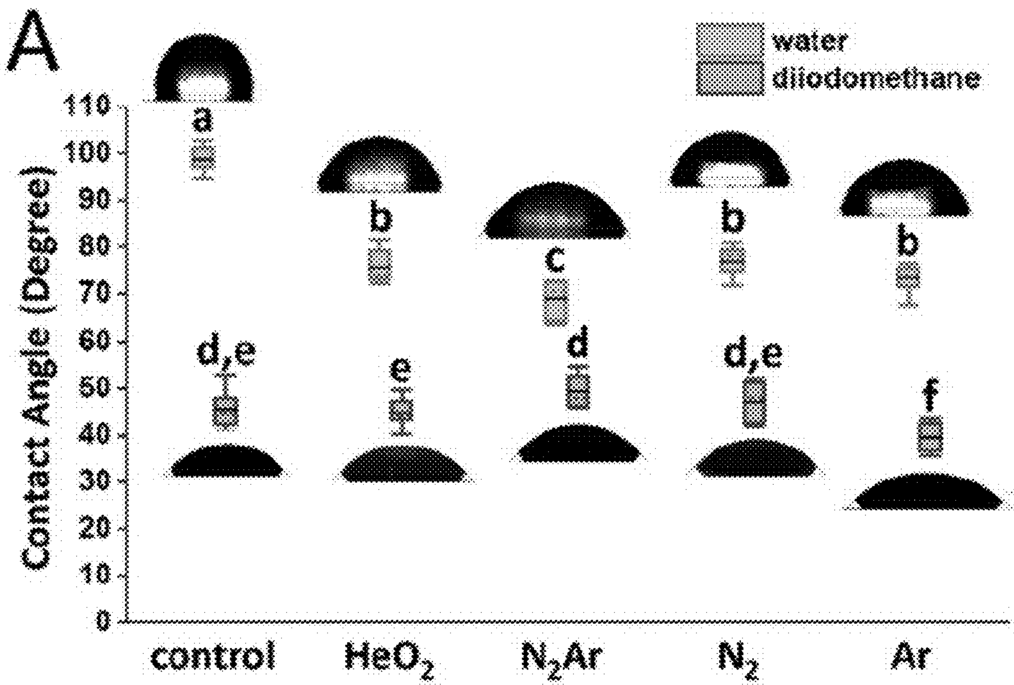
FIG. 1A relates to the contact angle of water and diiodomethane. The box plots represent the mean (black horizontal solid line), median (horizontal dashed line), interquartile range (box) and total range (whiskers) of the data set.
FIG. 1B shows the values of the total surface free energy ($\gamma^{total}$) dispersive component ($\gamma^d$) and polar component ($\gamma^P$) of each plasma-treated zirconia specimen. The same letters indicate that the values are not significantly different between plasma types ($p>0.05$). The error bars represent the standard deviation.

Hereinafter, the present invention will be described in detail.

Unless defined otherwise, all technical and scientific terms used in the present specification have the same meaning as commonly understood by one of ordinary skill in the art to which the present invention pertains. In general, the nomenclature used in the present specification is well known and commonly used in the art.

Plasma surface treatment can enhance clinical performance by modifying the chemical inertness properties of zirconia. The present invention determined the effects of plasma composition on the physicochemical surface modification of 3 mol % yttria stabilized tetragonal zirconia polycrystal (3Y-TZP). Low-temperature atmospheric plasma discharge was performed at an application distance of 10 mm for 60 seconds by using plasma composed of four different types of gases: $He/O_2$, $N_2/Ar$, $N_2$ and Ar. The static contact angle was measured to define the surface free energy. The elemental composition, surface crystallinity and surface morphology changes were evaluated by X-ray photoelectron spectroscopy (XPS), X-ray diffraction (XRD), confocal laser scanning electron microscopy (CLSM), and scanning electron microscopy (SEM), respectively. All plasma-treated specimens showed a significant decrease in water contact angle, and the lowest water contact angle (69°) was confirmed in the specimen treated with a plasma $N_2/Ar$ mixed gas. A lower contact angle indicates a higher surface hydrophilicity. CLSM and SEM analyses confirmed that no morphological changes were observed in all plasma-treated specimens. XPS analysis confirmed that the specimen treated with the plasma $N_2/Ar$ mixed gas showed a significant increase in O content and a decrease in surface C content, which are the causes of high surface hydrophilicity, compared to other plasma-treated specimens. XRD analysis confirmed changes in crystal size and microscopic deformation due to oxygen atom substitution in the specimen treated with the plasma $N_2/Ar$ mixed gas. That is, the treatment of the plasma $N_2/Ar$ mixed gas can contribute to enhancing the binding performance and bioactivity of 3Y-TZP by controlling the plasma-generated nitrogen function.

Mixing a molecular gas with chemically inert gases such as helium, neon and argon can change the plasma discharge dynamics and exhibit better biological performance. In the case of $N_2$ plasma, dissociation is very difficult due to the strong triple bond between two N atoms. One study reported that adding argon (Ar) to $N_2$ plasma enhanced the generation of active species through Pennig excitation and ionization depending on the Ar concentration in $N_2Ar$ plasma, and another study reported that metastable nitrogen molecules were formed by using plasma composed of $N_2$ and Ar. Another study reported that the discharge voltage of $N_2Ar$ plasma decreased rapidly compared to pure Ar gas even when a small amount of nitrogen (1%) was added to Ar. In the present invention, $N_2Ar$ plasma containing 10% nitrogen was used, and while irradiating the zirconia surface with the $N_2Ar$ plasma mixed gas, nitrogen atoms were replaced by oxygen atoms such that the zirconia surface tended to have more negative charges. Helium plasma can easily cause stable glow discharge with the addition of an active gas such as $O_2$, $N_2$ or $CF_4$, but since helium is much lighter than air, active oxygen species cannot easily reach the target material, and unlike helium, argon has a higher density than air, and thus, excited atomic oxygen can easily be transferred to the substrate.

Therefore, the present invention relates to a method for treating the surface of zirconia for dental use, which includes the following steps from one perspective:

(a) preparing zirconia which is stabilized with 1 to 5 mol % (preferably, 3 mol %) of yttria; and (b) generating plasma composed of a mixed gas of nitrogen and argon ($N_2/Ar$) and irradiating the plasma to the zirconia.

In the present invention, the argon is an inert gas, can be used at atmospheric pressure, and has the advantage of low operating costs. When argon gas is mixed with nitrogen gas, nitrogen molecules become nitrogen ions through the Penning ionization process. This means that ionization is possible even with a small amount of nitrogen gas mixed, and the maximum ionization effect can be obtained with a 10% nitrogen mixture, but the present invention is not limited thereto. The ionized nitrogen ions attack the oxygen pores on the zirconia surface to accelerate the surface anionization of the zirconia surface and create zirconium oxynitride to increase surface reactivity. Zirconia has a disadvantage of surface inactivity, but the plasma treatment method of the present invention using a mixed gas of nitrogen and argon ($N_2/Ar$) induces the generation of zirconia-nitride on the surface, and increases the ion conductivity of zirconia. Accordingly, zirconia treated with a plasma composed of a mixed gas of nitrogen and argon ($N_2/Ar$) by the above method can be characterized as being particularly optimal for dental materials.

In the present invention, the nitrogen and argon gases may be included at a component ratio of 0.3:9.7 to 1.5:8.5, preferably, 0.7:9.3 to 1.2:8.8, and more preferably, 1:9, but the present invention is not limited thereto.

From another perspective, the present invention relates to zirconia for dental use whose surface is treated by the above method.

From still another perspective, the present invention relates to a dental material including the zirconia as an active ingredient.

Although zirconia has surface inertness and low adhesiveness, by activating the zirconia surface by treating plasma composed of a mixed gas of nitrogen and argon ($N_2$/Ar) by the method of the present invention, the usability of zirconia as a material for dental implants, crowns, inlays, posts and orthodontic brackets can be enhanced.

Accordingly, the dental material may be characterized as being used to manufacture at least one dental article selected from the group consisting of an implant, a crown, an inlay, a post and an orthodontic bracket, but the present invention is not limited thereto.

Hereinafter, the present invention will be described in more detail through examples. These examples are intended only to illustrate the present invention, and it is apparent to those skilled in the art that the scope of the present invention is not to be construed as being limited by these examples.

Statistical Analysis

Statistical significance of the data was assessed by one-way analysis of variance (ANOVA) with Tukey's honesty significant differences (HSD) post hoc test at $\alpha$=0.05. All analyses were performed by using statistical software (IBM SPSS Statistics, v25.0, IBM Corp., Chicago, IL, USA).

EXAMPLE

Example 1

Specimen Preparation and Plasma Surface Treatment

Figure 7:
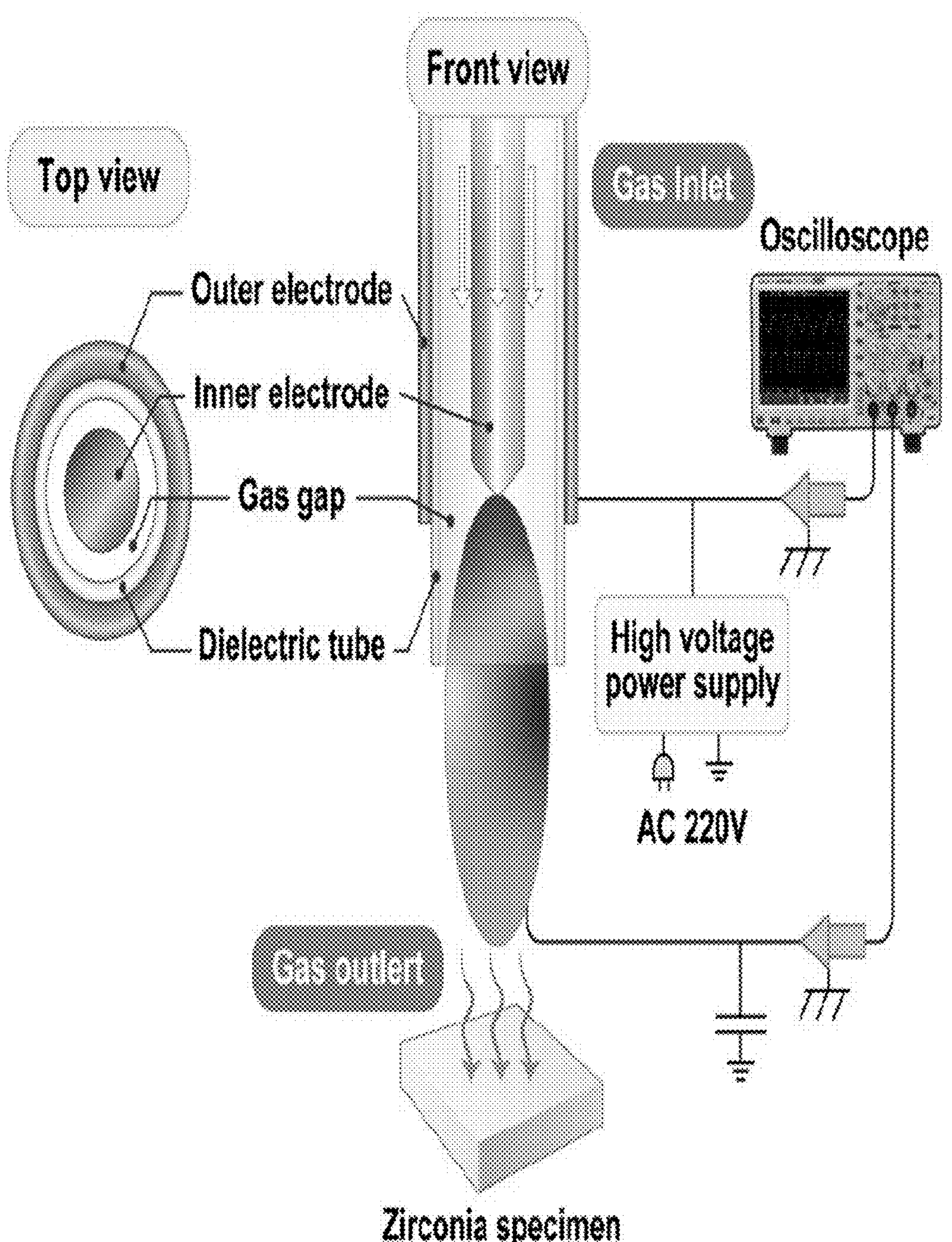
FIG. 7 is a schematic diagram of the experimental setup for treating the surface of zirconia specimens with plasma.

The present invention used 3Y-TZP (KATANA ML, Kuraray Noritake Dental, Osaka, Japan) which was sintered at 1,500° C. for 2 hours. A total of 140 plate-shaped specimens (10.0 mm×10.0 mm×1.0 mm) were prepared and polished to a uniform finish with 800 grit SiC paper. After ultrasonic cleaning for 20 minutes, plasma irradiation was performed at room temperature by using a low-temperature atmospheric pressure DBD plasma generator (PR-ATO-001, ICD Co., Anseong, Gyeonggi-do, Korea). The plasma was applied vertically to the specimen surface at a distance of 10 mm for 60 seconds. A schematic diagram of the device used in the experiment is as shown in FIG. 7. All specimens were randomly assigned to five groups (n=28), four of which were treated with plasma composed of four different types of gases (Ar, $N_2$, $N_2$/Ar mixture (10% nitrogen/90% argon) and He/$O_2$ mixture (15% helium/85% oxygen)), and one group without plasma treatment was used as a control. The input voltage was fixed at 5 kV using a high-voltage transformer, and the operating frequency was set to 25 kHz using a digital oscilloscope (MSO4032, Tektronix, Beaverton, OR, USA). The mass flow controller maintained a constant gas flow rate of 10 standard liters per minute (slm).

Example 2

Confirmation of Surface Contact Angle and Surface Free Energy Changes Due to Plasma Treatment The surface wettability of the specimens was measured by using a contact angle measuring device (Phoenix 300 Touch, S.E.O., Suwon, Gyeonggi-do, Korea). The contact angle was measured by using the sessile drop technique at room temperature and 60% relative humidity using distilled water (n=10) and nonpolar diiodomethane (n=10), and all measurements were performed at the center of the specimens.

The surface free energy was calculated by measuring the contact angle of the two liquids (distilled water and nonpolar diiodomethane) according to the Owens-Wendt equation. The total surface free energy ($\gamma^{total}$), including the dispersive component ($\gamma^d$) and the polar component ($\gamma^P$), was calculated.

FIG. 1A shows the contact angles along with the sessile drop images and $\gamma^{total}$, $\gamma^d$ and $\gamma^P$ values (FIG. 1B) of zirconia specimens that were treated with plasma composed of different types of gases, and the measured contact angles are listed in Table 1. After exposure to plasma, all specimens showed a significant decrease in the water contact angle, and the lowest value of 69° was measured in the specimen treated with plasma composed of a mixed gas of nitrogen and argon gas ($N_2$/Ar). The diiodomethane contact angles remained almost constant in all plasma-treated specimens except for argon (Ar) (FIG. 1A and Table 1). The total surface energy increased significantly in all specimens after plasma treatment, which mainly coincided with the increase in $\gamma^p$ values, and the $\gamma^P$ values increased the most in the specimen treated with plasma composed of a mixed gas of nitrogen and argon gas ($N_2$/Ar) (FIG. 1B).

TABLE 1

Measurement results of contact angles of water and diiodomethane on the surfaces of zirconia specimens treated with plasma composed of different types of gases.

| Plasma group | Contact Angle (°) | |
|---|---|---|
| | Water | Diiodomethane |
| Control | 98.75 ± 2.70[a] | 45.66 ± 4.30[d, e] |
| $HeO_2$ | 75.59 ± 3.38[b] | 44.72 ± 3.16[e] |
| $N_2$Ar | 69.00 ± 3.98[c] | 49.39 ± 3.33[d] |
| $N_2$ | 76.86 ± 3.30[b] | 47.21 ± 4.14[d, e] |
| Ar | 73.22 ± 3.00[b] | 39.60 ± 3.19[f] |

In Table 1, means with the same superscript in each column are not significantly different from each other according to Tukey's honest significant difference post hoc test (p>0.05).

Example 3

Confirmation of Surface Chemical Changes Due to Plasma Treatment by X-Ray Photoelectron Spectroscopy (XPS)

The elemental compositions of zirconia specimens treated with plasma composed of different types of gases were analyzed by X-ray photoelectron spectroscopy (XPS) (K-alpha, Thermo Fisher Scientific Inc., Waltham, MA, USA) by using a monochromatic Al K$\alpha$ X-ray source (1486.6 eV) at 12 kV and 3 mA (n=1). In addition, data were collected and core-level spectra were analyzed by using software (Thermo Avantage v5.980, Thermo Fisher Scientific Inc., Waltham, MA, USA). All XPS spectra were calibrated to the C is peak at 284.6 eV.

Figure 2A:
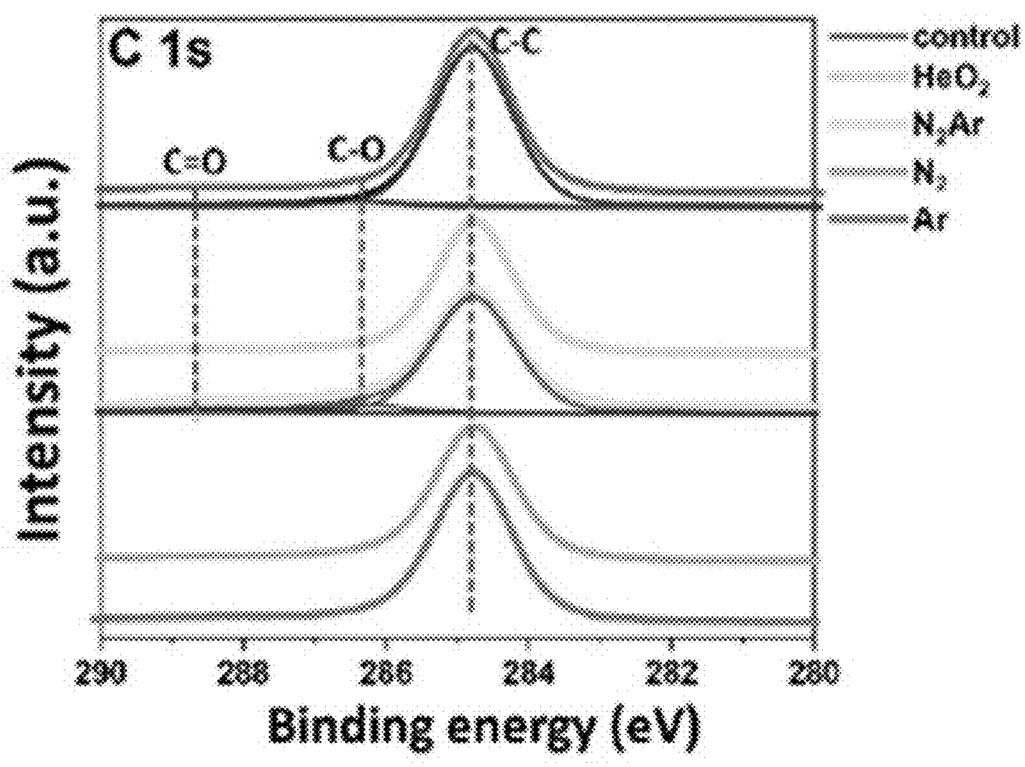
FIG. 2A relates to the carbon (C Is) XPS spectrum (X-ray diffraction).
Figure 2B:
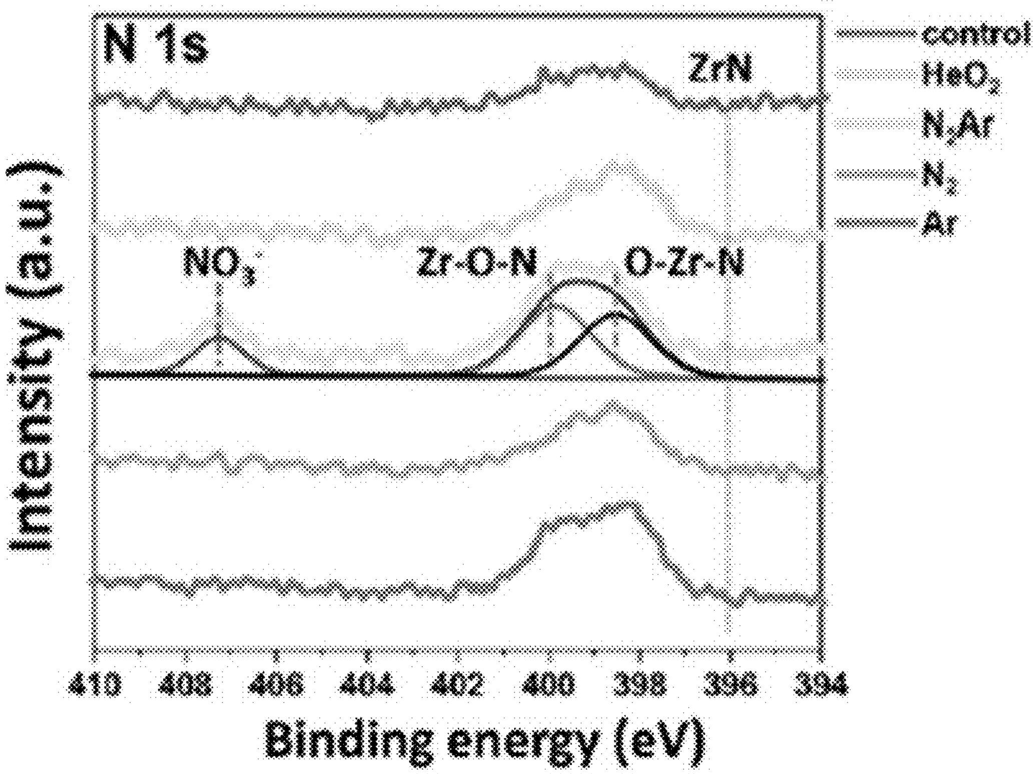
FIG. 2B relates to the nitrogen (N 1s) XPS spectrum. It was confirmed that a new component related to the presence of nitrate ($NO_3^-$) species in $N_2/Ar$-treated zirconia exhibited a binding energy of 406.5 eV.
Figure 2C:
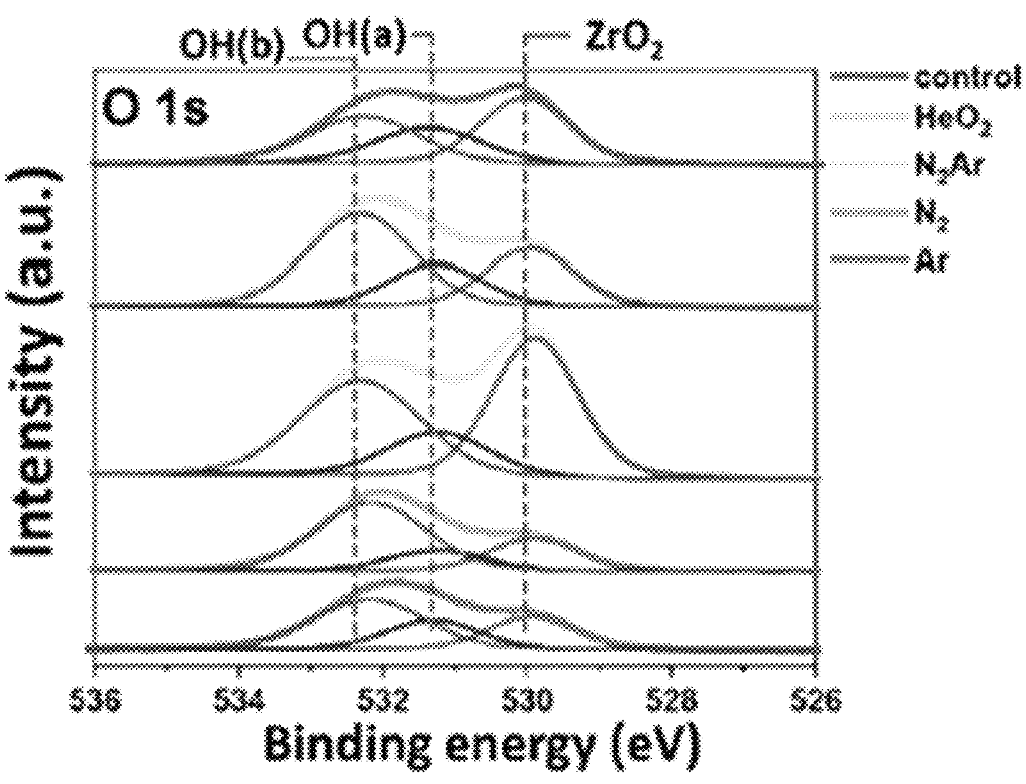
FIG. 2C relates to the oxygen (O 1s) XPS spectrum.
Figure 2D:
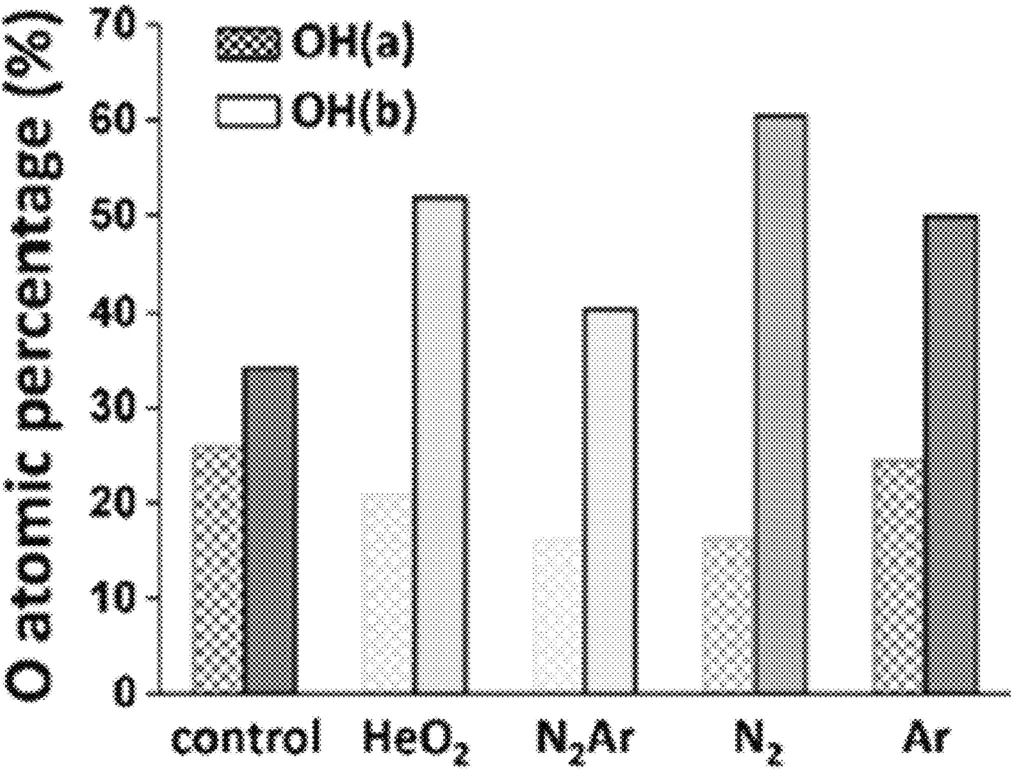
FIG. 2D relates to the percentage area of acidic hydroxyl groups OH (a) and basic hydroxyl groups OH (b) in the O 1s XPS spectrum.
Figure 2E:
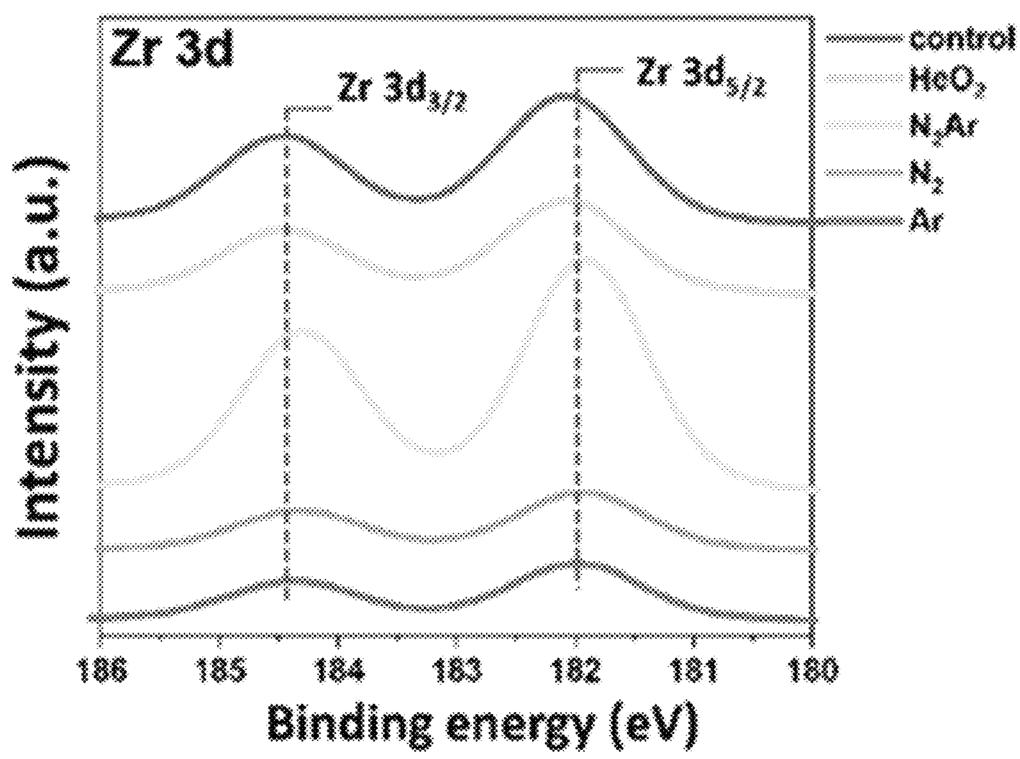
FIG. 2E relates to the zirconia (Zr 3d) XPS spectrum.
Figure 2F:
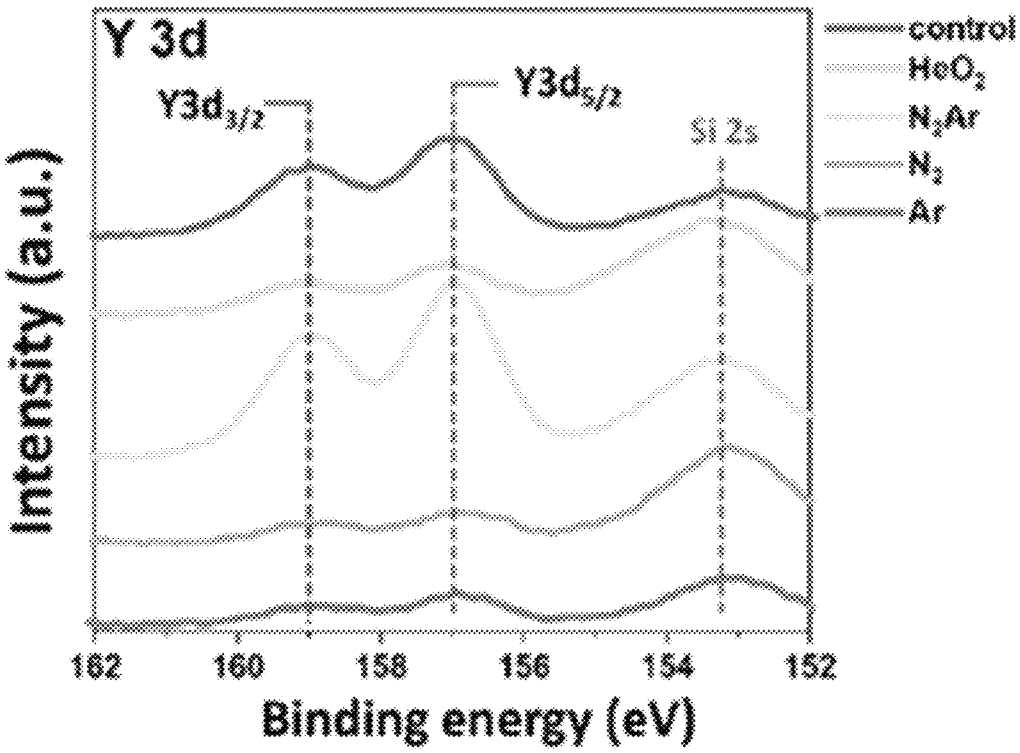
FIG. 2F relates to the Y 3d XPS spectrum for the outermost surface of zirconia which was treated with plasma including different kinds of gases.
Figures 3A, 3B:
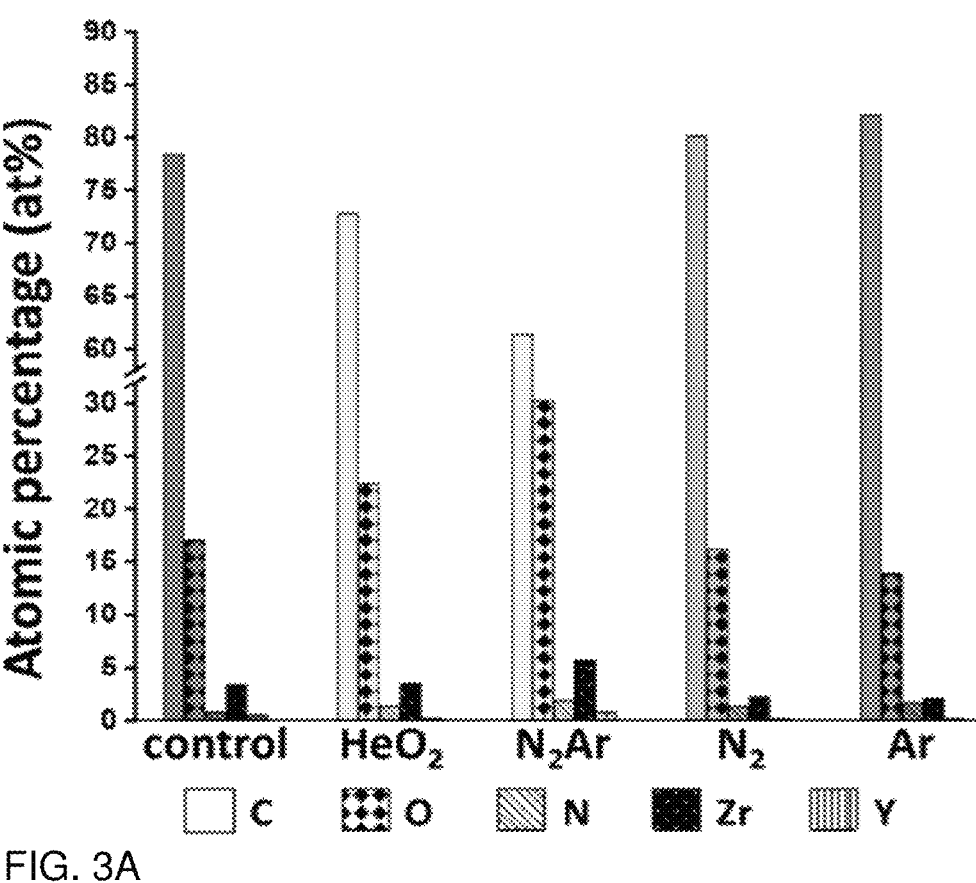
FIG. 3A relates to the atomic percentage (at %) of each element detected in zirconia which was treated with plasma including different kinds of gases.
FIG. 3B shows the nitrogen (N) concentration of zirconia treated with plasma composed of different types of gases.
Figure 3C:
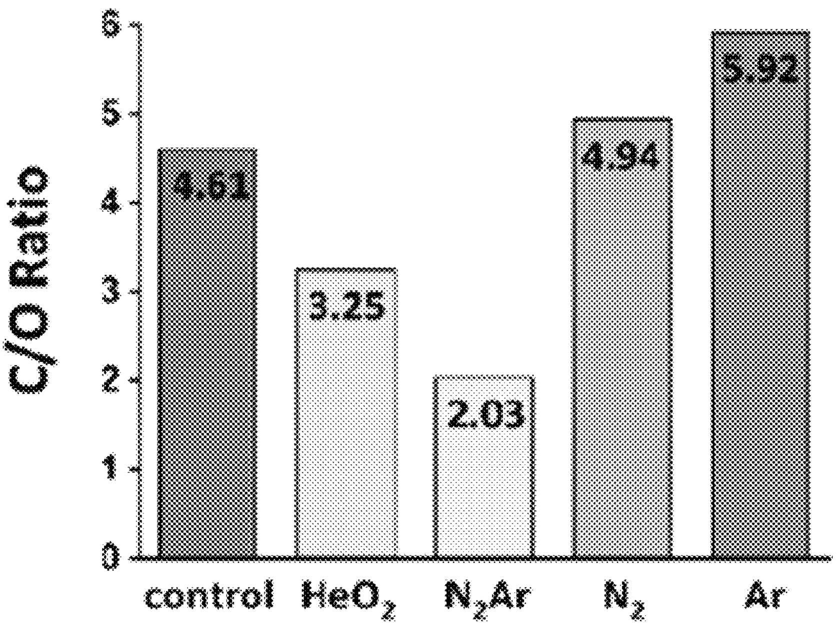
FIG. 3C shows the carbon/oxygen ratio of zirconia treated with plasma composed of different types of gases.

FIGS. 2A-2F show the XPS C 1s, O 1s, N 1s, Y 3d, and Zr 3d core level spectra, and FIGS. 3A-3C show the atomic percentages (at %) of these elements and the carbon/oxygen ratios of all specimens determined by XPS. In all specimens, the nitrogen content on the zirconia surface increased after plasma treatment, but was only in the range of 1 to 2% (FIGS. 3A and 3B). In all of the specimens treated with the plasma composed of a mixed gas of nitrogen and argon ($N_2$/Ar) and the specimens treated with a plasma mixed gas of helium and oxygen (He/$O_2$), the oxygen content increased, and the carbon content decreased. Additionally, in the specimen treated with the plasma composed of a mixed gas of nitrogen and argon ($N_2$/Ar), the carbon (C) content decreased the most, and the oxygen (O) content increased the most (FIG. 3A). The carbon/oxygen ratio was the lowest in the specimen treated with the plasma composed of a mixed gas of nitrogen and argon ($N_2$/Ar). This is thought to be related to the fact that the surface hydrophilicity increased the most in the specimen treated with the plasma composed of a mixed gas of nitrogen and argon ($N_2$/Ar), which generated a high level of oxygen-based radicals (FIG. 3C).

Unlike the specimens treated with other plasmas, nitrate ($NO_3^-$) species were formed on the surface of the zirconia in the specimen treated with the plasma composed of a mixed gas of nitrogen and argon gas ($N_2$/Ar). Nitrate anions can generate highly reactive nitrate radicals (NO3), and nitrate radicals can react with organic compounds due to their high diffusivity in nonpolar solvents, which can enhance the bioactivity or binding efficiency of 3Y-TZP. Therefore, this can enhance the bioactivity or binding efficiency of 3Y-TZP. The N is photoelectron region (FIG. 2B) shows a new component associated with the presence of nitrate ($NO_3^-$) species at a binding energy of 406.5 eV. Nitrogen atoms (N) can be adsorbed on the zirconia surface to form nitrogen-containing functional groups. The second component appearing at a binding energy of about 399.1 eV is related to the typical bonding state of nitrogen in $ZrO_xN_y$ or zirconium oxynitride, which can identify nitrogen in the zirconia lattice. N-doped zirconium oxynitride products were confirmed in all specimens without direct $N_2$ supply, and the highest intensity was shown in the specimen treated with plasma composed of a mixed gas of nitrogen and argon ($N_2$/Ar) (FIGS. 2C and 3B). It is thought that the interaction of the surrounding air and the zirconia surface during plasma treatment was involved. The plasma nitridation of zirconia can produce a ZrN structure, which is characterized by high hardness, even harder than 3Y-TZP, high resistance to wear or corrosion, and high thermal stability. The nitridation of zirconia is the replacement of oxides with nitrides, and the lattice structure of zirconium oxynitride is slightly deformed from the ideal cubic structure, which was also confirmed in the present invention.

The carbon content of the zirconia surface exposed to plasma composed of different types of gases is as shown in FIG. 2A. The carbon content was significantly reduced in the specimen treated with plasma composed of a mixed gas of nitrogen and argon ($N_2$/Ar) compared to the specimens treated with other plasma gases. This indicates that the zirconia surface treated with plasma composed of a mixed gas of nitrogen and argon ($N_2$/Ar) is less susceptible to carbon contamination when treated in air thereafter. The dominant carbon species detected in XPS were generally associated with airborne carbon contaminants that make the surface hydrophobic. The organic compounds remaining on the surface were removed by breaking the C—C bonds during plasma treatment. In the specimens treated with plasma composed of a mixed gas of nitrogen and argon ($N_2$/Ar), the C—C bonds of hydrocarbons are broken by the collision cross-section between N and Ar or excited to a metastable state, thereby forming new functional groups (such as C—O and C═O bonds) that can enhance the hydrophilicity of the surface. Unlike the specimens treated with other plasmas, the specimens treated with plasma composed of a mixed gas of nitrogen and argon ($N_2$/Ar) were confirmed to have a larger amount of C—O species, which is related to the higher $\gamma^p$ value. The $\gamma^P$ component of surface energy has a more important effect on cell interaction than yd. Considering the most noticeable changes in the contact angle and $\gamma^P$ component observed in the specimens treated with plasma composed of a mixed gas of nitrogen and argon ($N_2$/Ar), it indicates that the plasma composed of a mixed gas of nitrogen and argon ($N_2$/Ar) can significantly enhance the bioactivity of zirconia specimens.

Partially stabilized zirconia suitable for dental applications can be obtained by adding 1 to 5 mol % (preferably, 3 mol %) (5.2 wt. %) of a low valence oxide such as yttria. The oxygen vacancies compensate for the charge imbalance and increase the ionic conductivity of the zirconia material. The O 1s spectrum consists of broad features that can be resolved into three components: the oxygen of $ZrO_2$ (OL) at about 530.0 eV, the oxygen of the acidic hydroxyl group OH (a) at about 531.5 eV, and the oxygen of the basic hydroxyl group OH (b) at about 532.5 eV (FIG. 2B). The surface hydroxyl groups can be formed by dissociation at the specimen surface in the presence of moisture in the air. Therefore, the content of surface hydroxyl groups can increase when the surface provides adsorption sites for $H_2O$ due to oxygen deficiency. The relatively high OL-to-OH intensity ratio observed in the specimens treated with plasma composed of a mixed gas of nitrogen and argon ($N_2$/Ar) indicates that the dissociative adsorption energy of $H_2O$ is relatively lower in the specimens treated with plasma composed of a mixed gas of nitrogen and argon ($N_2$/Ar) than in the specimens treated with plasma composed of other types of gases, which is due to the formation of surface oxynitride through partial nitridation of $ZrO_2$ in the specimens treated with plasma composed of a mixed gas of nitrogen and argon ($N_2$/Ar) (FIG. 2B). However, all of the specimens showed an increase in basic hydroxyl groups OH(b) (FIG. 2D), which suggests that the plasma treatment leaves defects on the surface for dissociative $H_2O$ adsorption. One study reported that OH(b) may play a more important role than OH(a) in enhancing the bioactivity of a substrate because primary proteins are easily attracted to positively charged surfaces.

The XPS spectrum of the Zr 3d spectrum (FIG. 2E) clearly showed two characteristic components of Zr $3d_{3/2}$ at 181.3 eV and Zr $3d_5s_2$ at 183.6 eV, which can correspond to zirconium in the $Zr^{4+}$ state ($ZrO_2$). In the Y 3d spectrum (FIG. 2F), two components of Y3d (Y$3d_{3/2}$ and Y$3d_{5/2}$) for the oxidized yttrium in the $Y^{3+}$ state were identified. The prominent Y 3d appearing in the specimen treated with the plasma composed of a mixed gas of nitrogen and argon ($N_2$/Ar) can be regarded as the result of grain refinement of the microstructure.

Example 4

Confirmation of Crystallinity Change Due to Plasma Treatment Through X-Ray Diffraction (XRD) and Rietveld Analysis One specimen was submitted from each specimen treated with plasma composed of different types of gases to determine the crystal structure and phase transformation. X-ray powder diffraction (XRD) patterns were recorded at room temperature on a DMAX-2200PC X-ray diffractometer (Rigaku, Tokyo, Japan) by using monochromatic CuKα1 radiation ($\lambda$=1.5406 Å). Data were collected in the 2θ range of 20 to 90 with a step size of 0.02 and a step time of 4 s/step. Quantitative phase analysis was performed by the Rietveld refinement method implemented in the Fullprof program.

In particular, changes in the crystallite size and lattice strain induced by plasma treatment were determined by Williamson-Hall (W-H) analysis using the following formula: where β is the integral breadth or full width at half maxima, D is the crystallite size, K is the shape factor (0.9), and ε is the strain.

$$\beta_{hkl}\cos\theta = K\lambda/D + 4\varepsilon\sin\theta \quad \text{(Formula 1)}$$

The phase composition ratio and lattice parameter for specimens treated with plasma composed of different types of gases were calculated, and the results are shown in Table 2. Before plasma irradiation (control), the zirconia phase was observed to be the major phase, tetragonal phase (t-$ZrO_2$) and cubic phase (c-$ZrO_2$). Through Rietveld analysis, it was confirmed that the cubic phase content decreased and the metastable tetragonal (t') phase content increased in the specimens treated with plasma composed of a mixed gas of nitrogen and argon ($N_2$/Ar) and nitrogen ($N_2$). In all specimens, the formation of the metastable tetragonal phase (t'-$ZrO_2$) was confirmed (maximum 3 wt. %) after plasma treatment. This may be due to the oxygen atom displacement induced in the zirconia crystal structure during plasma irradiation.

TABLE 2

Rietveld analysis results for phase composition and lattice parameters of zirconia specimens treated with plasma composed of different types of gases

| Plasma Group | Phase | Amount (wt. %) | Lattice Parameters a = b (Å) | c (Å) | c/a Ratio |
|---|---|---|---|---|---|
| Control | t | 62(2) | 3.6069(2) | 5.1777(4) | 1.0151 |
| | c | 38(2) | 5.1382(3) | 5.1382(3) | |
| $HeO_2$ | t | 59(2) | 3.6070(2) | 5.1788(4) | 1.0152 |
| | t' | 2(1) | 3.625(2) | 5.173(5) | 1.0091 |
| | c | 39(1) | 5.1383(3) | 5.1383(3) | |
| $N_2Ar$ | t | 67(2) | 3.6098(2) | 5.1808(4) | 1.0148 |
| | t' | 3(1) | 3.626(2) | 5.175(5) | 1.0092 |
| | c | 30(1) | 5.1423(3) | 5.1423(3) | |
| $N_2$ | t | 66(2) | 3.6087(2) | 5.1804(4) | 1.0151 |
| | t' | 3(1) | 3.626(1) | 5.172(3) | 1.0086 |
| | c | 31(1) | 5.1407(3) | 5.1407(3) | |
| Ar | t | 60(2) | 3.6075(2) | 5.1779(4) | 1.0149 |
| | t' | 2(1) | 3.625(2) | 5.173(6) | 1.0091 |
| | c | 38(1) | 5.1390(3) | 5.1390(3) | |

In Table 2, t represents tetragonal zirconia (space group $P4_2$/nmeS), t' represents metastable tetragonal zirconia (space group $P4_2$/nmcZ), and c represents cubic zirconia (space group Fm3m). The values in parentheses correspond to the estimated standard deviation of the left-most significant number. c/a ratio=c(Å)√v2 a(Å).

Figure 4A:
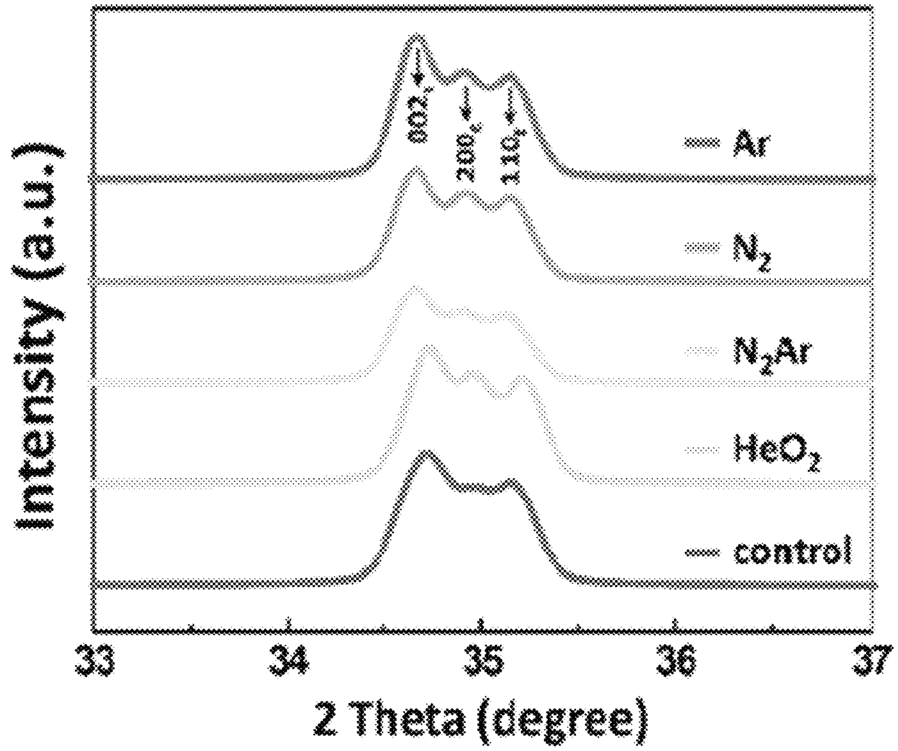
FIGS. 4A-4B relate to the XRD spectra of zirconia specimens treated with plasma composed of different types of gases in the range of $2\theta=33$ to 37° (FIG. 4A) and $2\theta=58$ to 62° (FIG. 4B). In addition, FIG. 4C relates to the Williamson-Hall (W-H) plot of $\beta \cos \theta$ versus $4 \sin \theta$ on the tetragonal system calculated from the XRD spectra.
Figure 4B:
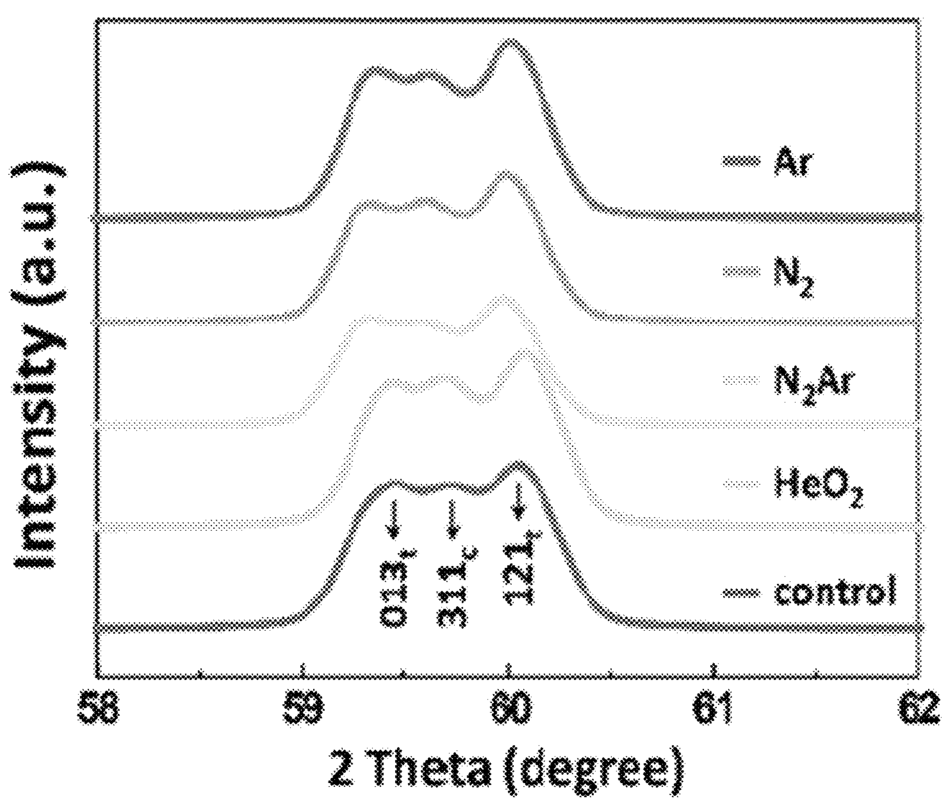
Figure 4C:
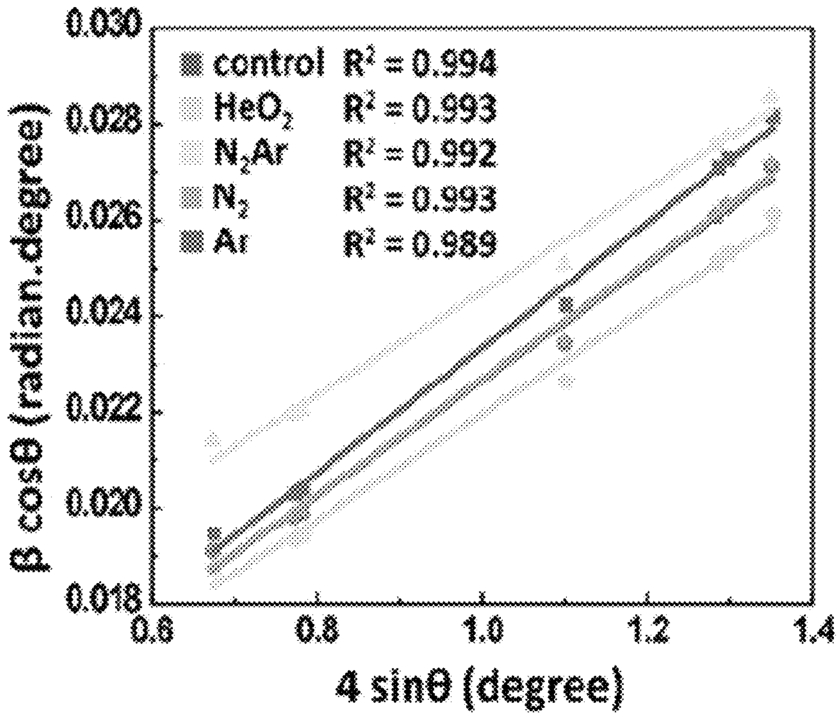

The powder XRD patterns and W—H plots of the specimens are shown in FIGS. 4A-4C. All detected peaks corresponded to the tetragonal and cubic phases, and no clear monoclinic phase was observed. Analysis of the XRD peaks shows that the tetragonal peak was slightly broadened in the specimen treated with a plasma composed of a mixed gas of nitrogen and argon ($N_2$/Ar) (FIGS. 4A and B). This suggests that the contribution is due to changes in the crystal size and lattice strain. The slope and y-intercept of the W—H plot were estimated by using the Scherrer equation to compare the strain and grain size. Since a positive slope indicates tensile strain, the development of compressive strain can be estimated from the flat slope of the specimen treated plasma composed of with a mixed gas of nitrogen and argon ($N_2$/Ar). The decrease in crystal size due to lattice shrinkage and compressive strain in the specimen treated with plasma composed of a mixed gas of nitrogen and argon ($N_2$/Ar) may contribute to the peak broadening. The crystal sizes were measured to be 87.5 nm (control), 83.2 (He/$O_2$), 65.1 ($N_2$/Ar), 85.4 ($N_2$) and 85.5 (Ar). Plasma nitridation of 3Y-TZP may play an important role in improving mechanical properties by inducing lattice strain through crystal deformation and increasing damage resistance.

Example 5

Confirmation of Surface Morphology Changes Due to Plasma Treatment

The three-dimensional (3-D) surface characteristics were analyzed by using a confocal laser scanning microscope (CLSM; LEXT OLS3000, Olympus, Tokyo, Japan) at a magnification of 50X over an area of 256×192 $\mu m^2$ (n=5). Surface texture parameters, particularly the arithmetic mean height Sa; root mean square height Sq; and maximum pit height Sv, were calculated according to ISO 25,178. Surface analysis was performed independently at two central locations, and a total of 10 measurements were made for each specimen treated with plasma composed of different types of gases.

The surface microstructures of the specimens were evaluated by using a scanning electron microscope (SEM; JSM-7800F Prime, JEOL, Tokyo, Japan) at an acceleration voltage of 5.0 kV and a working distance (WD) of 6.0 mm at magnifications of 3000×, 10,000× and 30,000× (n=1).

Figure 5:
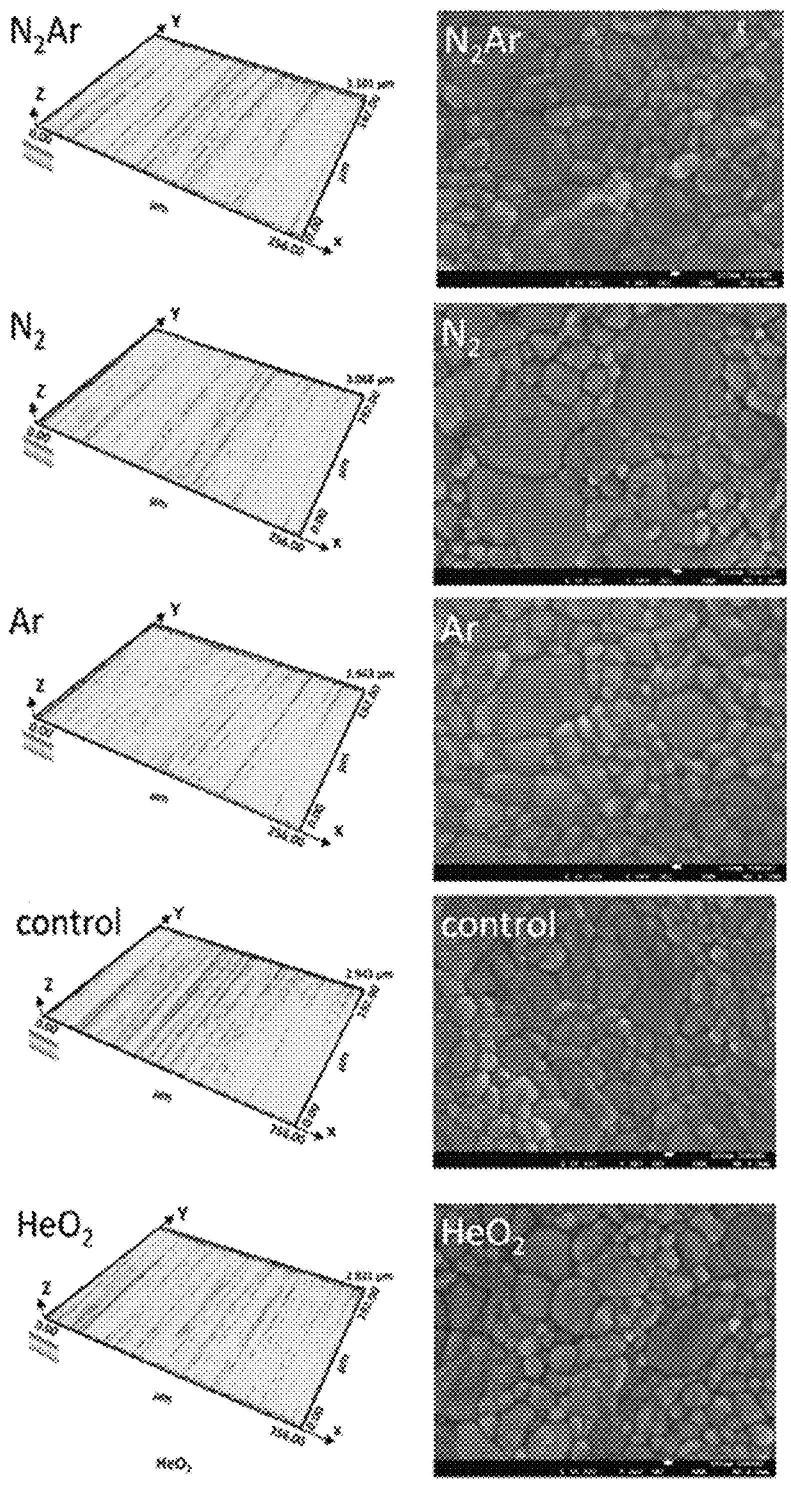
FIG. 5 shows representative 3D images obtained by confocal laser scanning microscopy (left) and scanning electron microscopy image at 30,000× magnification (right) of zirconia specimens treated with plasma composed of different types of gases.
Figure 6:
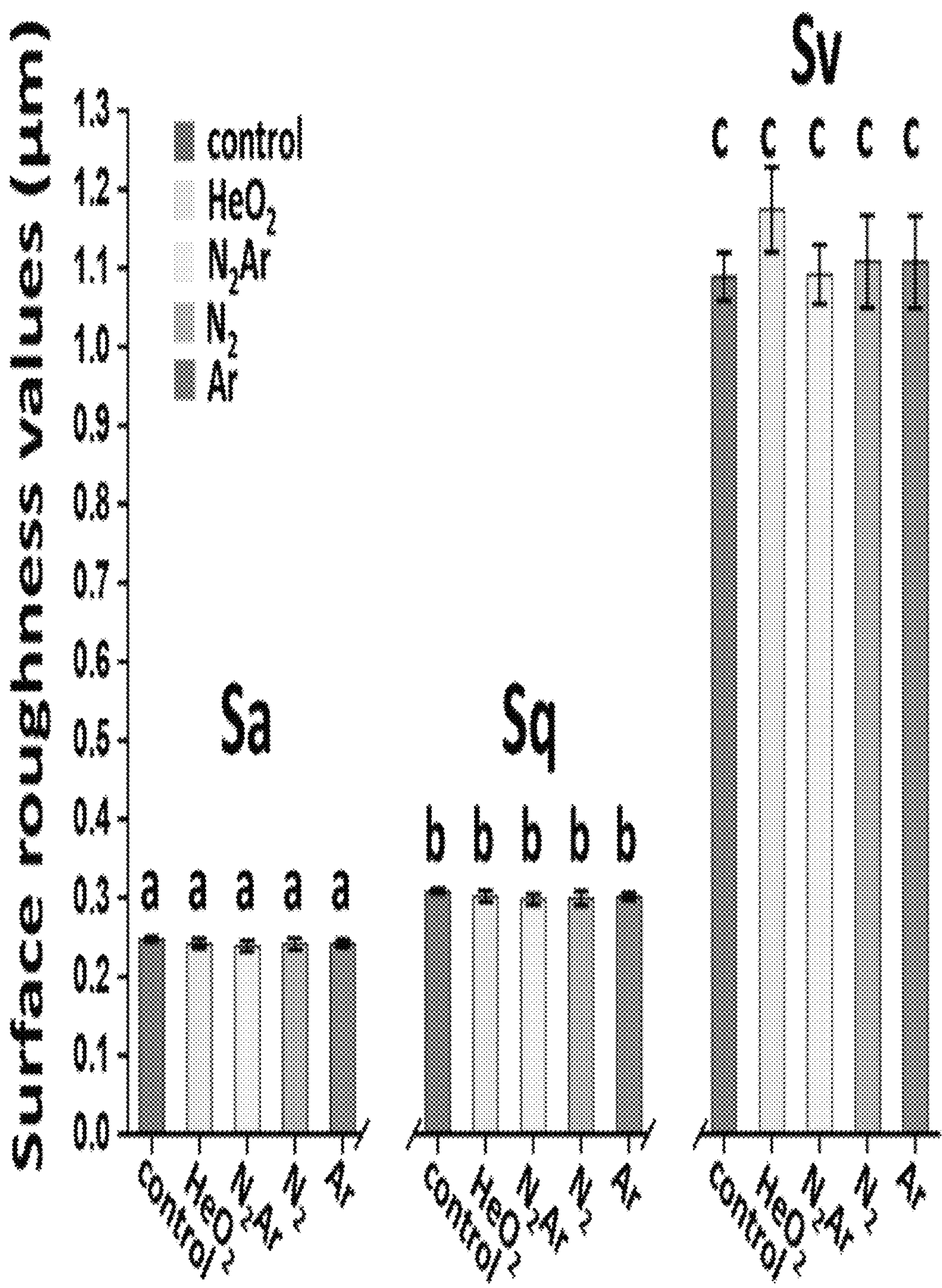
FIG. 6 relates to the surface texture parameters (Sa, Sq and Sv) of zirconia specimens treated with plasma composed of different types of gases. The same letters indicate that the Sa, Sq and Sv values are not significantly different ($p>0.05$).

The enlarged confocal and SEM images of the specimens treated with plasmas composed of different types of gases are shown in FIG. 5. The surface texture parameters (Sa, Sq, Sv) measured by CLSM are shown in FIG. 6. The morphological differences were not significant, and all the specimens exhibited relatively similar microstructures characterized by large cubic crystals and integrated tetragonal symmetry without relevant surface damage.

The invention claimed is:

1. A method for treating the surface of zirconia for dental use, comprising the steps of:

(a) preparing zirconia which is stabilized with 1 to 5 mol % of yttria; and (b) generating plasma composed of a mixed gas of nitrogen and argon ($N_2$/Ar) and irradiating the surface of the zirconia with the mixed gas to reduce carbon content and increase oxygen content on the surface of the zirconia as compared to untreated zirconia, thereby increasing hydrophilicity of the zirconia.

2. The method of claim 1, wherein in step (b) above, the plasma comprises nitrogen and argon gases at a component ratio of 0.3:9.7 to 1.5:8.5.

3. Zirconia for dental use whose surface is treated by the method of claim 2, wherein the surface of the zirconia has a reduced carbon content and an increased oxygen content compared to untreated zirconia.

4. A dental material, comprising the zirconia of claim 3 as an active ingredient.

5. The dental article of claim 4, wherein the dental article is at least one selected from the group consisting of an implant, a crown, an inlay, a post and an orthodontic bracket.

6. Zirconia for dental use whose surface is treated by the method of claim 1, wherein the surface of the zirconia has a reduced carbon content and an increased oxygen content compared to untreated zirconia.

7. A dental material, comprising the zirconia of claim 6 as an active ingredient.

8. A dental article comprising the dental material of claim 7, wherein the dental article is at least one selected from the group consisting of an implant, a crown, an inlay, a post and an orthodontic bracket.

* * * * *